(12) United States Patent
Kovensky

(10) Patent No.: US 8,821,461 B2
(45) Date of Patent: Sep. 2, 2014

(54) PATIENT GOWN FOR A MEDICAL TREATMENT FACILITY

(75) Inventor: Cynthia Kovensky, Kissimmee, FL (US)

(73) Assignee: Capstone Manufacturing LLC, Kissimmee, FL (US)

( * ) Notice: Subject to any disclaimer, the term of this patent is extended or adjusted under 35 U.S.C. 154(b) by 11 days.

(21) Appl. No.: 13/525,704

(22) Filed: Jun. 18, 2012

(65) Prior Publication Data

US 2013/0131617 A1 May 23, 2013

Related U.S. Application Data

(60) Provisional application No. 61/561,420, filed on Nov. 18, 2011.

(51) Int. Cl.
*A61M 1/00* (2006.01)
*A61F 5/44* (2006.01)
*A41D 13/12* (2006.01)

(52) U.S. Cl.
CPC .......... *A41D 13/1281* (2013.01); *A61F 5/4408* (2013.01); *Y10S 2/901* (2013.01)
USPC .............. 604/327; 2/114; 2/113; 2/115; 2/50; 2/52; 2/51; 2/48; 2/88; 2/104; 2/901; 2/75; 2/80; 2/111

(58) Field of Classification Search
CPC ........... A61M 1/00; A61F 5/44; A41D 13/12; A41D 13/10; A41B 13/10; A41B 13/08; A41B 9/00; A41B 9/06
USPC .................................................. 604/317, 327
See application file for complete search history.

(56) References Cited

U.S. PATENT DOCUMENTS

| | | | |
|---|---|---|---|
| 4,649,572 A * | 3/1987 | Roessler | 2/49.2 |
| 6,460,187 B1 * | 10/2002 | Siegel | 2/114 |
| 6,694,522 B1 | 2/2004 | Neal | |
| 7,181,773 B1 | 2/2007 | Piraka | |
| 7,424,750 B2 | 9/2008 | Kerr | |
| 2008/0000006 A1 * | 1/2008 | Ochoa et al. | 2/114 |
| 2008/0168592 A1 | 7/2008 | Silver | |
| 2009/0172862 A1 | 7/2009 | Sheward | |
| 2010/0235963 A1 | 9/2010 | Haydon | |
| 2010/0242150 A1 | 9/2010 | Trouillot | |

* cited by examiner

*Primary Examiner* — Tatyana Zalukaeva
*Assistant Examiner* — Ilya Treyger
(74) *Attorney, Agent, or Firm* — Cian G. O'Brien, Esq.; Beusee Wolter Sanks & Maire, P.A.

(57) ABSTRACT

A full coverage gown that is used in medical facilities is presented. The gown includes a urine catheter pocket affixed to the gown. The gown also includes a pair of ties affixed to the gown above the urine catheter pocket. The pair of ties is configured to loop and tie around a hook attached to a urine catheter bag to prevent a backflow of urine and to secure the urine catheter bag within the catheter pocket.

15 Claims, 4 Drawing Sheets

PATIENT GOWN FOR A MEDICAL TREATMENT FACILITY

CROSS-REFERENCE TO RELATED APPLICATIONS

This application claims the benefit of U.S. Provisional Application No. 61/561,420 filed Nov. 18, 2011, which is incorporated by reference herein in its entirety.

FIELD OF THE INVENTION

The invention relates to treatment of patients in medical treatment facilities and, more specifically, to a gown design for a patient in a medical treatment facility, such as a hospital.

BACKGROUND OF THE INVENTION

Medical treatment facilities, such as hospitals, which practice in-patient care, routinely require that the patient stay at the hospital for extended periods of time during their treatment and rehabilitation following the treatment. During these extended periods, the patient changes out of their clothes, and is issued a standard hospital gown. Conventional hospital gowns have several shortcomings, as discussed herein. For example, it is not uncommon for patients to require a urine catheter, which is attached to a urine catheter bag. While the patient is bedridden, the urine catheter bag has a hook which is secured to the patient's bed rail. However, when the patient is out of bed and walking, such as during recovery and rehabilitation from surgery or illness, the patient must walk while holding their urine catheter bag. As a result, injury risk factors to the patient are elevated, such as a risk of falling as the patient attempts to maneuver multiple drains and tubes while walking. In another example, after surgery, drains and tubing are used to drain excess fluid from the surgical site/wound and are secured to the body with tape to prevent dislodging. The drains and tubing must be taped to the patient's body, which can be uncomfortable while walking and painful while attaching and detaching the tape from the patient's body. In yet another example, conventional hospital gowns are routinely worn backwards, with an opening at the back, and thus provide little to no coverage of the patient's backside, thereby providing no dignity to the patient. For proper coverage of the patient's body, two hospital gowns are often required to be used and worn in reverse orientations, thereby increasing costs to the hospital.

BRIEF DESCRIPTION OF THE INVENTION

One embodiment of the present invention provides a medical treatment facility gown, including a urine catheter pocket affixed to the gown. The gown further includes a pair of ties affixed to the gown above the urine catheter pocket. The ties are configured to loop around a hook attached to the urine catheter bag, to keep the urine catheter bag raised and prevent urine backflow out of the urine catheter bag. The urine catheter bag is secured, concealed and contained in the catheter pocket.

Another embodiment of the present invention provides a medical treatment facility gown, including a snap fastener affixed to the gown at an attachment point, where the snap fastener is secured to opposing sides of the attachment point. The snap fastener is passed through the hook attached to a top of the urine catheter bag, to secure the urine catheter bag to the attachment point.

Another embodiment of the present invention provides a medical treatment facility gown, including a urine catheter pocket affixed to the gown. The gown further includes a fastener affixed to the gown, where the fastener is configured to loop around the hook of the urine catheter bag positioned above the urine catheter pocket, to secure the catheter bag within the catheter pocket.

BRIEF DESCRIPTION OF THE DRAWINGS

The invention is explained in the following description in view of the drawings that show.

DETAILED DESCRIPTION OF THE INVENTION

The embodiments of the present invention are directed to a gown to be worn by patients within a medical treatment facility, such as a hospital, a nursing home, or any medical treatment facility which provides in-patient care. Indeed, the gown design may also be used by a patient during treatment at their residence or at any non-medical treatment center where in-patient care may be provided, for example. Although the embodiments of the present invention discussed below mention the specific example of a patient being treated within a hospital, this is merely exemplary and does not limit the scope of the present invention as encompassing a gown design which may be worn by any patient receiving in-patient treatment at any medical treatment facility.

FIGS. 1-6 illustrate exemplary embodiments of a gown 10, which may be a reversible full coverage gown. The exemplary embodiments address the shortcomings of the conventional hospital gowns discussed above. The inventor of the present invention recognized that conventional hospital gowns do not include any structural features to secure, contain and conceal a urine catheter bag or surgical drains and tubing. Accordingly, the inventor of the present invention designed a hospital gown which addresses these notable shortcomings of the conventional hospital gown.

Figures 1, 2:
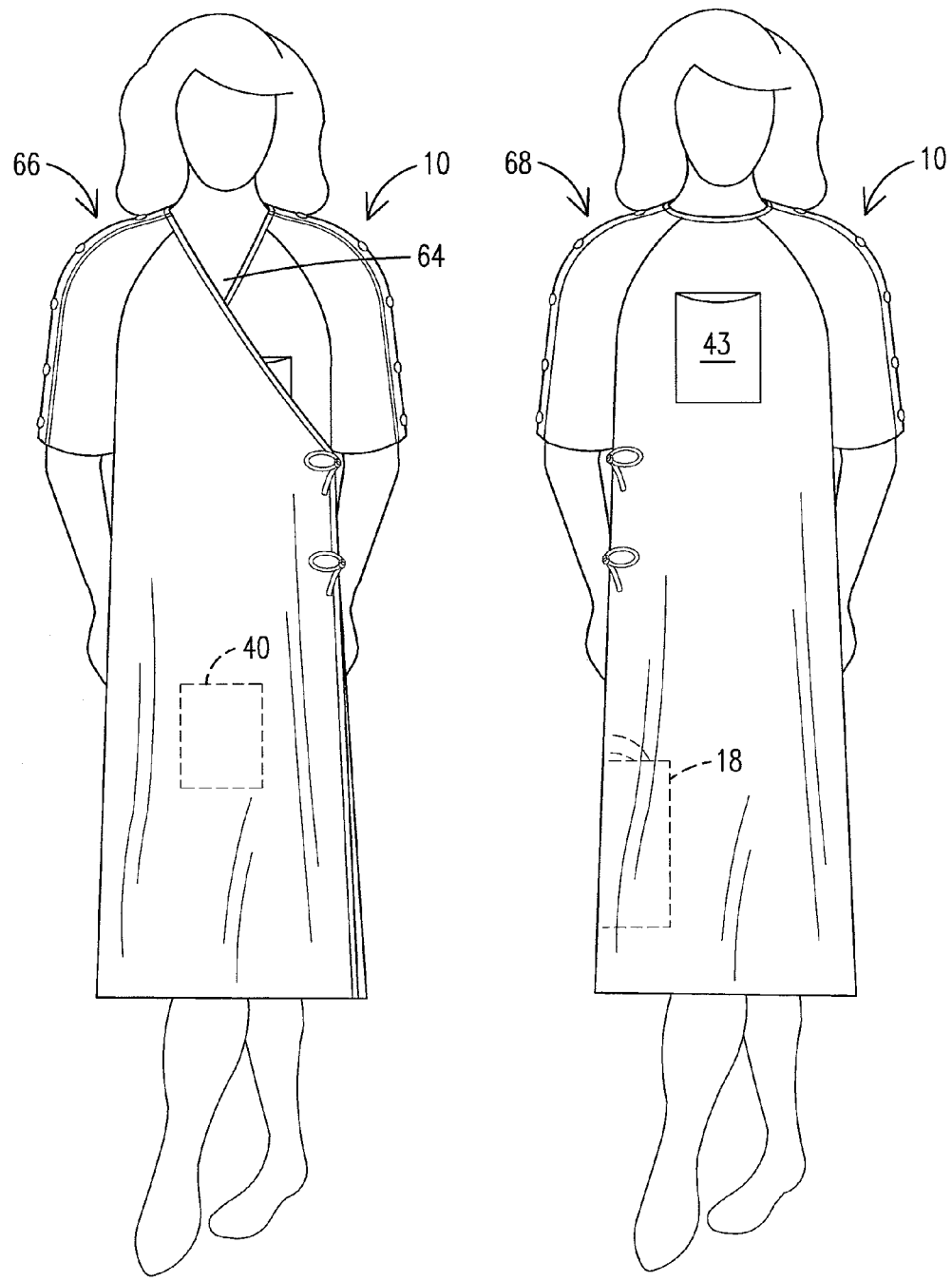
FIG. 1 is a front plan view of a patient gown worn in a forward orientation.
FIG. 2 is a front plan view of the patient gown of FIG. 1 worn in a reverse orientation.

As illustrated in FIGS. 1-2, the gown 10 may be worn in a forward orientation 66 (FIG. 1) or a reverse orientation 68 (FIG. 2). However, as discussed below, although the patient could wear the gown 10 in the reverse orientation 68, it is preferred that the patient wear the gown 10 in the forward orientation 66, unless the patient is unable to get out of bed, such as in an Intensive Care Unit (ICU) setting, for example.

Figure 3:
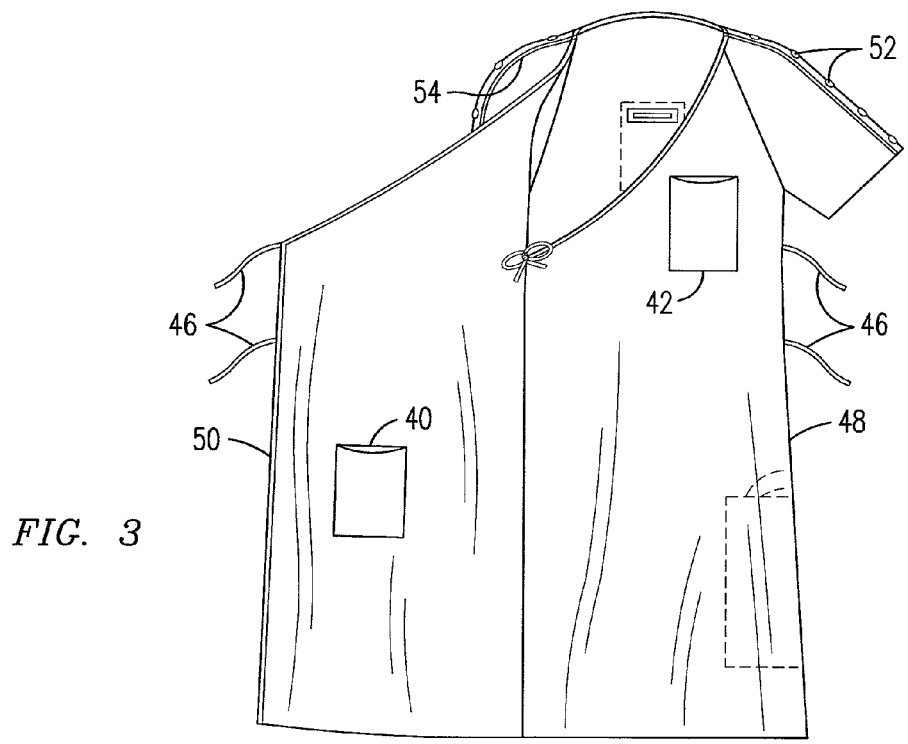
FIG. 3 is a front plan view of the patient gown of FIG. 1 with an open right panel.
Figure 4:
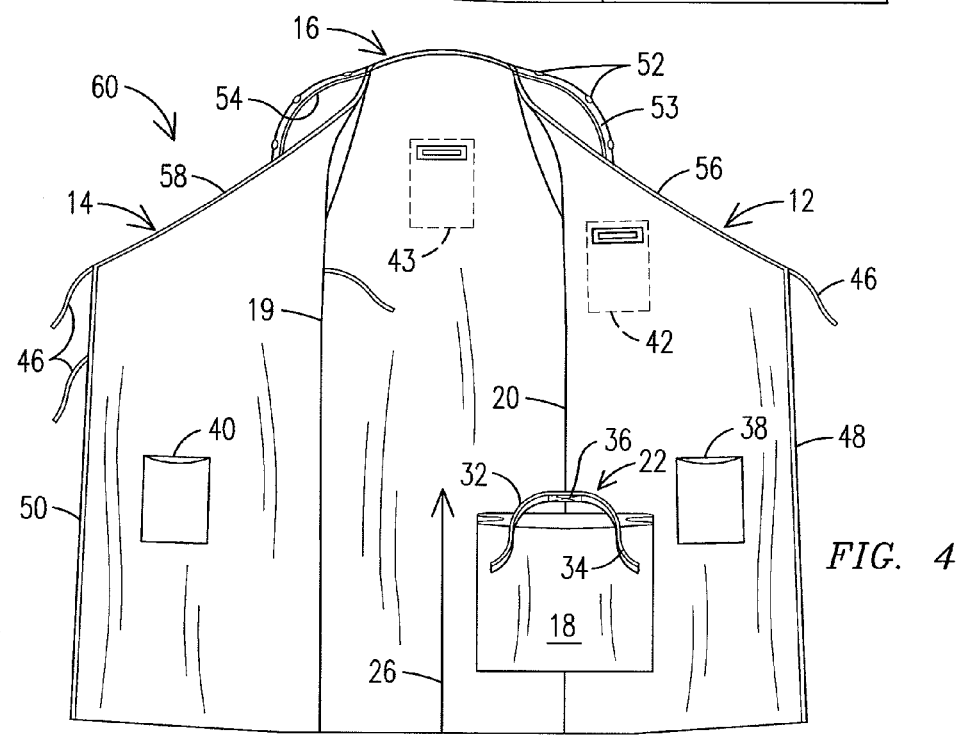
FIG. 4 is a front plan view of the patient gown of FIG. 1 with open right and left panels.

As illustrated in FIGS. 3-4, the gown 10 includes panels, namely a left panel 12, a right panel 14 with a center panel 16 between the left panel 12 and the right panel 14, where the left panel 12 and right panel 14 are based on the perspective of the patient wearing the gown. When the gown 10 is worn in the forward orientation 66, the center panel 16 is positioned over or against the patient's back, while when the gown 10 is worn in the reverse orientation 68, the center panel 16 is positioned over or against the patient's chest and stomach region. The left panel 12 is linked to the center panel 16 along a left seam 20, and the left panel 12 is configured to fold over the center panel 16, along the left seam 20, as illustrated in FIG. 3. The right panel 14 is linked to the center panel 16 along a right seam 19, and the right panel 14 is configured to fold over the center panel 16, along the right seam 19, as illustrated in FIG. 1.

Figure 5:
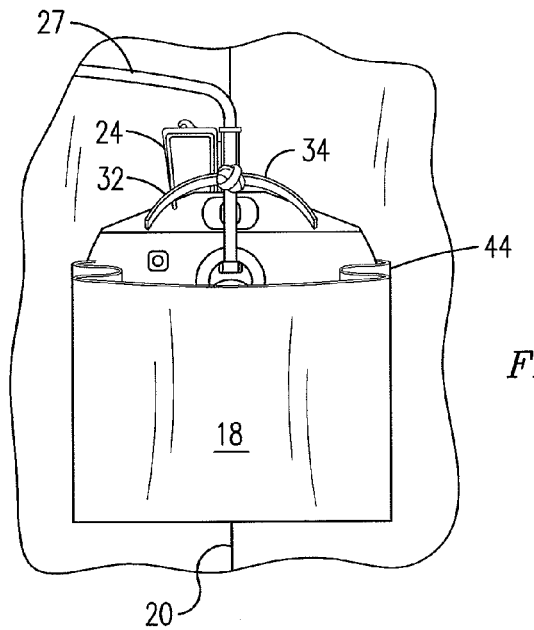
FIG. 5 is a partial view of a urine catheter bag secured within a urine catheter pocket of the patient gown of FIG. 4.
Figure 6:
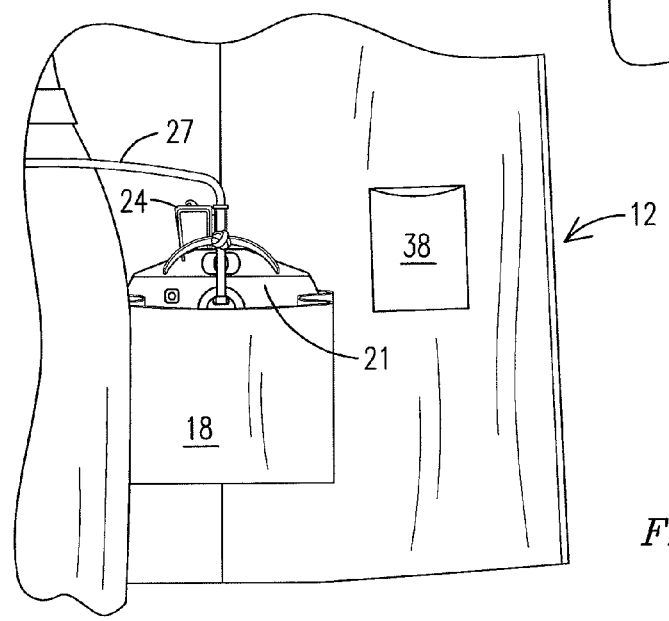
FIG. 6 is a front plan view of the patient gown of FIG. 1 with an open left panel.

As further illustrated in FIG. 4, a urine catheter pocket 18 is affixed along the left seam 20 between the left panel 12 and the center panel 16. In a preferred embodiment, the urine catheter pocket 18 is centered along the left seam 20. However, the pocket 18 need not be centered along the left seam 20. A fastener 22 is also affixed to the left seam 20, above the urine catheter pocket 18, and the fastener 22 includes a center region 36 which is sewn into the left seam 20, as well as a pair of ties 32,34 that are positioned above the urine catheter pocket 18. As illustrated in FIG. 5, once a urine catheter bag 21 is positioned within the urine catheter pocket 18, the pair of ties 32,34 are looped and tied around a hook 24 attached to the urine catheter bag 21, which is raised above the urine catheter pocket 18. In an exemplary embodiment, the ties 32,34 are self-fastened or tied to each other, upon looping the ties 32,34 around the hook 24. Since the ties 32,34 are positioned above the urine catheter pocket 18, the ties 32,34 are used to secure the urine catheter bag 21 at a location above the urine catheter pocket 18, in order to prevent backflow of urine and/or the bag 21 from collapsing or folding over within the pocket 18. As illustrated in FIG. 5, the urine catheter pocket 18 has an expandable side 44, with foldings arranged like an accordion, such that the volume of the urine catheter pocket 18 is expandable as the urine catheter bag 21 fills, to prevent constriction of the urine catheter bag 21 and backflow of urine from out of the urine catheter bag 21 up through the catheter tube 27 (FIG. 6). In an exemplary embodiment, the urine catheter bag 21 is a Foley® catheter bag with dimensions of approximately 11.5 inch length×11.5 inch width, and the urine catheter pocket 18 is sized to fit the Foley® catheter bag with dimensions of approximately 13 inch length×13 inch width. The above dimensions of the Foley® catheter bag and the catheter pocket that is sized to fit the Foley® catheter bag are merely exemplary, the embodiments of the invention is not limited to this specific size catheter bag and pocket and thus may include any size catheter bag and catheter pocket which is sized to accommodate the catheter bag.

Although the embodiment of the gown 10 discusses that the fastener 22 and the urine catheter pocket 18 are secured along the left seam 20, the fastener and urine catheter pocket may be secured to any attachment point along the gown surface, such as the right seam 19, for example, or any attachment point other than the right seam 19 and left seam 20, for example, provided that the fastener with the ties are secured at a location above the urine catheter pocket. Additionally, although the embodiment of the gown 10 discusses that the fastener 22 includes ties 32,34 which are looped around the hook 24 attached to the urine catheter bag 21, to secure the urine catheter bag 21 within the urine catheter pocket 18, the fastener need not include a pair of ties, and the urine catheter bag need not include a hook, provided that the fastener includes a mechanism positioned above the urine catheter bag, to loop around the junction of the catheter tube and the urine catheter bag, to secure the urine catheter bag within the urine catheter pocket.

As further illustrated in FIG. 4, the fastener 22 includes the plurality of ties 32,34 that are positioned above the urine catheter pocket 18, so that the ties 32,34 are configured to loop and tie around the hook 24 attached to the urine catheter bag 21 at a vertical position 26 measured up to the region 36 from the base of the gown 10. The vertical position 26 at which the ties 32,34 are looped and tied or fastened around the hook 24 is specifically calculated to be above a threshold location to ensure that gravity will draw all flow from the urine catheter (not shown) into the urine catheter bag 21 and thus avoid unwanted backflow (FIG. 6). In an exemplary embodiment, the vertical position 26 is spaced approximately 22 inches from the base of the gown 10 to the region 36 and/or 20 inches from the base of the gown 10 to the top edge of the pocket 18. These exemplary numerical dimensions of the vertical position are merely one possible vertical position of the pocket along the left seam, and the embodiments of the present invention are not limited to this specific numerical dimension and may be selectively adjusted to any vertical position, provided that the vertical position at which the ties are looped and tied around the hook is attached to the urine catheter bag, to prevent the backflow of urine. Additionally, by positioning the urine catheter pocket 18 (and urine catheter bag 21) along the left seam 20, the urine catheter bag 21 will be secured out of a path of motion of the legs of a patient wearing the gown as they walk, to avoid abrasive contact with the urine catheter bag 21. Indeed, the urine catheter pocket 18 may be affixed at any horizontal position along the gown, provided that the catheter pocket 18 is out of the path of motion of the legs of the patient wearing the gown as they walk.

As further illustrated in FIG. 4, the gown 10 includes a surgical drain pocket 38 affixed to the left panel 12 and a surgical drain pocket 40 affixed to the right panel 14. The surgical drain pockets 38,40 are sized and configured to hold surgical drains and tubing which are routinely sutured and secured, post-surgery, for example. In an exemplary embodiment, for an extended period of time, the left surgical drain pocket 38 may be used to hold drains and tubing that extend from the surgical wound site on the left side of the patient's body, while the right surgical drain pocket 40 may be used to hold drains and tubing that extend from the surgical wound site on the right side of the patient's body. Thus, depending on the surgery performed at the site/location, the left surgical drain pocket 38 or right surgical drain pocket 40 may be used to hold the drains and tubing.

As further illustrated in FIGS. 3-4, a telemetry pocket 42 is affixed to a surface of the left panel 12, and is sized and configured to hold a telemetry monitor or personal items, such as notes or papers, if the patient is not on a telemetry monitor. The telemetry pocket 42 on the surface of the left panel 12 is concealed when the gown 10 is worn, by folding the right panel 14 over the left panel 12, to conceal the telemetry pocket 42 behind the right panel 14, as illustrated in FIG. 1. In addition to the telemetry pocket 42 discussed above, which is used when the gown 10 is worn in the forward orientation 66, the gown 10 is also provided with a second telemetry pocket 43, which is affixed to the center panel 16 of the gown 10 and is visible and used when the gown 10 is worn in the reverse orientation 68 (FIG. 2). Although the above embodiment of the invention discusses that the telemetry pocket is affixed to a surface of the left panel 12, the telemetry pocket may be affixed to a surface of any portion of the gown, provided that the telemetry pocket is positioned in a location where the telemetry monitor and other personal items of the patient can be placed and removed from the telemetry pocket.

Upon securing the urine catheter bag 21 in the urine catheter pocket 18, the drains and tubing in the drain pocket(s) 38,40, and the telemetry monitor in the telemetry pocket 42, the patient can walk hands-free without having to hold anything in their hands, other than pushing an IV (intravenous) pole or a walker if warranted, for example. Indeed, depending on the particular treatment of the individual patient, the patient may not have one of the drains and tubing, the urine catheter bag 21 or a telemetry monitor, as part of their individual treatment. The preferred embodiment of the gown 10 is made to accommodate all of these possible treatments, and thus provide a gown 10 which can accommodate a patient who uses the urine catheter bag 21, drains and tubing and the telemetry monitor by providing pockets to secure, contain and conceal all of these items in the gown 10 and walk around hands-free. Specifically, the urine catheter bag 21 is contained and concealed in the pocket 18, when the gown 10 is in the closed position (FIG. 1). Indeed, the bag 21 may be fully or partially concealed in the pocket 18 when the gown 10 is in the open position (FIG. 6). Additionally, if a patient does not require the use of the urine catheter bag 21, the drain and tubing, or the telemetry monitor, the gown 10 can still accommodate this patient, who can still wear the gown 10, and provide enhanced dignity to the patient while out of bed by providing coverage to their rear area as compared with conventional gowns, such as when the patient is walking during recovery and rehabilitation from surgery or illness, for example. Thus, even for those patients who do not require the use of drains and tubing, these patients can still use the gown 10 and appreciate the simplicity of applying and removing the gown 10, while maintaining dignity. In an exemplary embodiment, while the patient is bed bound, the gown 10 may be worn in the reverse orientation 68 to accommodate those who are bedridden and immobile. (FIG. 2).

Although the above embodiments of the present invention discuss that the gown 10 includes pockets to hold the urine catheter bag 21, the drains and tubing and the telemetry monitor, the present invention is not limited to this arrangement, and the gown may feature only some or none of these pockets, such as a gown design with the pocket to hold the urine catheter bag 21 and without the pocket for the drains and tubing, or a gown design with the pocket to hold the drains and tubing and without the pocket to hold the urine catheter bag 21. However, as discussed above, the embodiment of the gown 10 discussed above does feature the design in which pockets are provided to hold the urine catheter bag, the drains and tubing and the telemetry monitor.

As further illustrated in FIGS. 3-4, the gown 10 includes side ties 46 positioned along an outer edge 48 of the left panel 12, and an outer edge 50 of the right panel 14. Upon wearing the gown 10, the right panel 14 is folded over the left panel 12, and the side tides 46 of the right panel 14 are tied to the side ties 46 of the left panel 12 along a side of the body of the patient (FIGS. 1-2). The tying arrangement of the left and right panel 12,14 with the side ties 46 along the side of the patient's body ensures that surgical and wound dressings on the patient's body, such as dressings along the patient's center front, are adequately covered and protected by the overlapping left and right panel 12,14 covering their center front area. By positioning the ties 46 along a side of the patient's body, the ties 46 are positioned to prevent contact with a wound and thus prevent possible cross-contamination of the wound by the ties 46.

As illustrated in FIG. 4, the gown 10 further includes snaps 52 which each include a snap/button fastener and receiver arrangement on right and left sleeves, with openings 54 in between each snap 52. The gown 10 is designed such that the snaps 52 are adequately spaced such that the openings 54 are sized to allow an IV tube(s) to be passed through the openings 54 and within the interior of the gown 10, to secure the IV tube(s) to the patient wearing the gown 10, to pass IV fluids to the patient. During assembly of the gown 10, the snap/button arrangement of the snaps 52 are connected together along the top portion of the gown 10, to form the openings 54 in between each snap 52 or consecutive snaps 52. The snaps 52 are positioned along IV snap strip regions on the sleeves of the gown 10, which are color coded, for easy assembly of the gown 10. The snaps 52 may be positioned along the snap strip of the gown 10 that has a color, such as white, for example, while the remaining portions of the gown 10 has a color that is distinct from the color of the snap strip, such as blue, for example. Thus, providing easy assembly by user. And upon removing the gown 10 from a laundry machine, the gown 10 may be assembled by connecting the snaps 52 which are positioned along a color-coded snap strip region of the gown 10. Although the above discusses that the snaps 52 are positioned along a color-coded snap strip of the gown 10 and the remaining portion of the gown 10 is color-coded to distinguish the snap strip, the snap strip need not be color coded, and may share the same color as the gown 10. Additionally, the gown 10 need not include the snaps 52 and the openings 54, as discussed above, as the patient may be provided with IV fluids using an alternative route.

The left panel 12 has an upper edge 56 and the right panel 14 has an upper edge 58 that slants downward from the center panel 16 in an outward direction, when the gown is in the open position 60 (FIG. 4). Upon folding the right panel 14 over the left panel 12 in the closed position (FIG. 1), the upper edge 56 of the left panel 12 and the upper edge 58 of the right panel 14 form a V-shaped neck design 64 for the patient, which may decrease friction between the gown 10 and the IV insertion site, potentially decreasing the risk of possible infection. Upon folding the right panel 14 over the left panel 12 so that the gown 10 is in closed position (FIG. 1), the gown 10 can be partially opened by unfolding the right panel 14 and the left panel 12 to expose just the front portion of the patient, while maintaining the center panel 16 along a back of the patient, to perform treatment on the front portion of the patient, without removing the gown 10 from the patient.

The gown 10 is made from polyester material. In one example, the gown 10 is made from 100% polyester material which is an inherently strong and durable fabric, that naturally repels moisture, dries relatively fast, retains it shape with little fading and can withstand multiple cycles in industrial machines. In another example, the gown 10 is made from 50% polyester material and 50% cotton material. The gown 10 may be made from any proportion of polyester material and a remaining portion of cotton material, such as a majority proportion of polyester material and a remaining portion of cotton material. Alternatively, the gown 10 may be made from a non-polyester material. In an exemplary embodiment, the material used to make the gown 10 is chosen such that the gown 10 is approved by the medical center or hospital in which it is used, and is capable of withstanding multiple cycles through industrial type laundry machines used in most medical center facilities. However, the embodiment of the present invention is not limited to any particular material.

Figure 9:
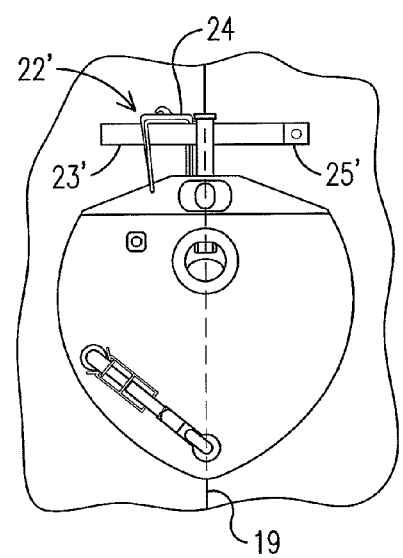
FIG. 9 is a partial view of a urine catheter bag secured to a fastener of the alternate patient gown of FIG. 8.
Figure 7:
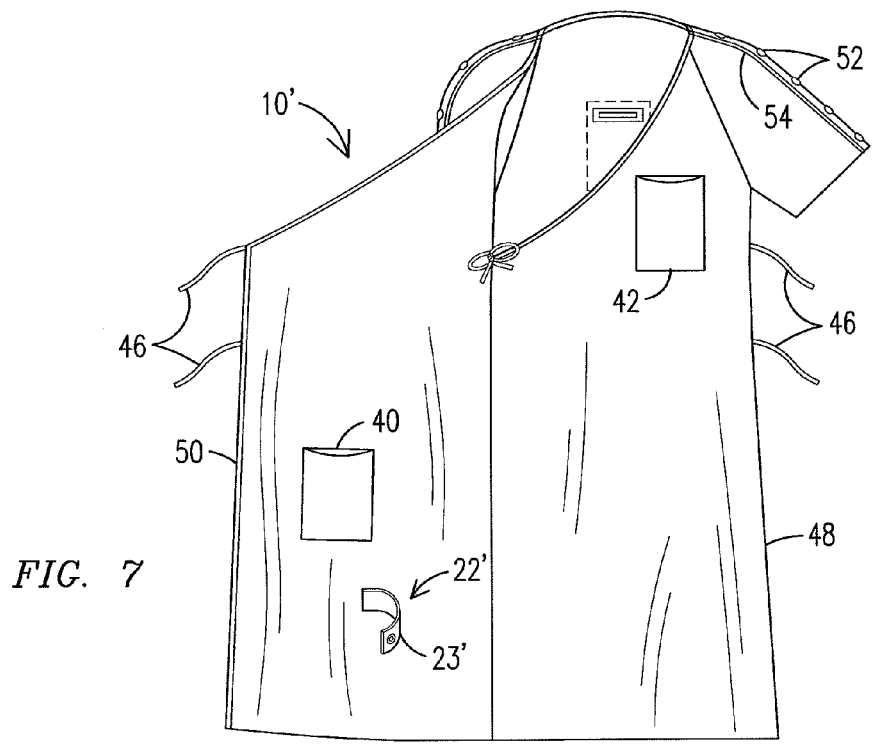
FIG. 7 is a front plan view of an alternate patient gown with an open right panel.
Figure 8:
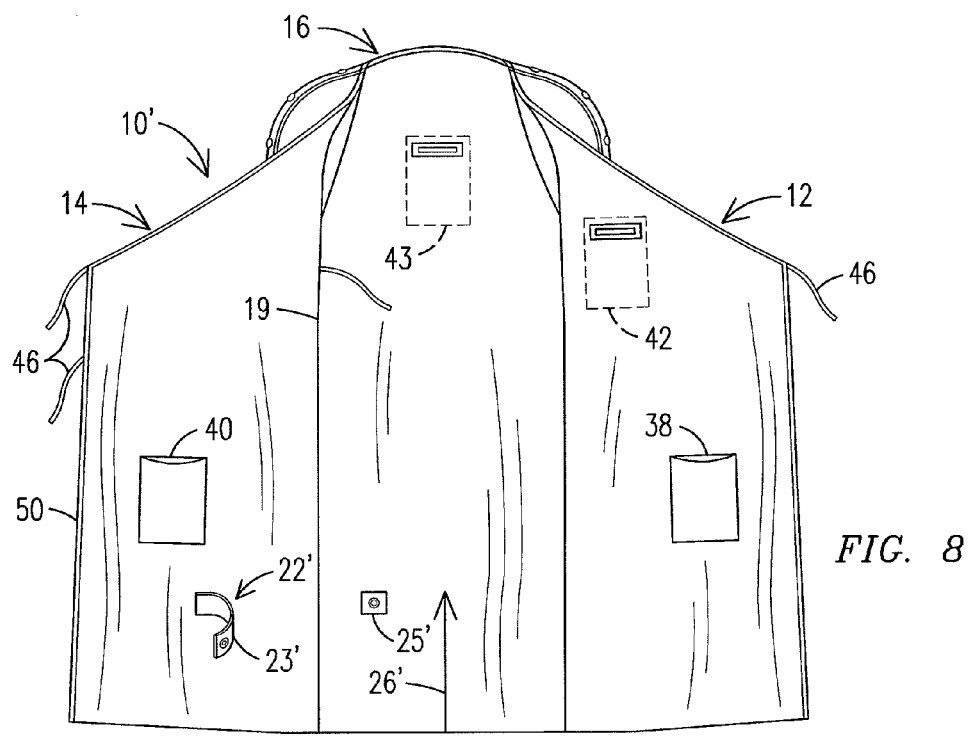
FIG. 8 is a front plan view of the alternate patient gown of FIG. 7 with open right and left panels.

FIGS. 7-9 illustrates an alternate hospital gown 10' which is similar to the hospital gown 10 discussed above of FIGS. 1-6, but includes some design variations, as discussed below. As illustrated in FIGS. 7-8, the gown 10' includes a fastener 22' affixed to a right seam 19 of the gown 10' between the right panel 14 and the center panel 16. The fastener 22' includes a strap 23' and snap/button receiving portion 25' to receive and hold the strap 23'. FIG. 9 illustrates that the urine catheter bag 21 is positioned along the right seam 19, after which the strap 23' is passed through the hook 24 at the top of the urine catheter bag 21, and the strap 23' is then secured to the snap/button receiving portion 25' on an opposite side of the right seam 19, to secure the urine catheter bag 21 to the hospital gown 10'. Unlike the gown 10 design above, where the urine catheter bag 21 is secured within a urine catheter pocket 18, the gown 10' design does not secure the urine catheter bag 21 within a pocket, but instead secures the urine catheter bag 21 to the fastener 22' attached to the right seam 19. The fastener 22' is positioned along the right seam 19, to secure the urine catheter bag 21 along the right seam 19, out of the movement path of the legs of the patient wearing the gown, as they walk. The fastener 22' is secured to the urine catheter bag 21 at a vertical position 26' which is above a threshold location along the right seam 19 to prevent backflow of urine. Those elements of the gown 10', depicted in FIGS. 7-9 not discussed herein, are similar to those equivalent-numbered elements of the gown 10 in FIGS. 1-6 discussed above, without prime notation, and thus require no further discussion herein. Although the gown 10' design above discusses that the fastener 22' is affixed along the right seam 19 of the gown 10', the fastener can be affixed to any attachment point along the surface of the gown, including the left seam 20 or any attachment point other than the right seam 19 or left seam 20, for example, provided that the fastener is secured to the urine catheter bag at a vertical position to prevent the backflow of urine.

FIG. 6 illustrates a front plan view of the patient gown 10 with an open left panel 12, exposing the left drain pocket 38, the urine catheter pocket 18, and the urine catheter bag 21 secured within the urine catheter pocket 18 with the fastener 22, as previously discussed. The gown 10,10' designs discussed above are sized according to a standard gown size, from a pediatric standard gown size to a bariatric standard gown size, for example. Although the gown is designed based on standard size(s), the gowns may also be designed based on custom size(s).

While various embodiments of the present invention have been shown and described herein, it will be obvious that such embodiments are provided by way of example only. Numerous variations, changes and substitutions may be made without departing from the invention herein. Additionally, while embodiments of the invention have been described with reference to an exemplary embodiment, it will be understood by those skilled in the art that various changes, omissions and/or additions may be made and equivalents may be substituted for elements thereof without departing from the spirit and scope of the invention. In addition, many modifications may be made to adapt a particular situation or material to the teachings of the invention without departing from the scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A medical treatment facility gown, comprising:
   a urine catheter pocket affixed to a surface of the gown facing an interior of the gown when the gown is in a closed position; and
   a pair of ties affixed to the gown surface above the urine catheter pocket, said ties configured to loop and tie around a hook attached to a urine catheter bag to hold up the urine catheter bag received within an opening of the pocket along the surface, to prevent urine backflow out of the urine catheter bag and to secure, conceal, and contain the urine catheter bag along the gown surface within the catheter pocket;
   a left panel;
   a right panel;
   a center panel positioned between the left panel and the right panel; and
   wherein the urine catheter pocket and the ties are affixed to the gown surface along a seam between one of the left panel or the right panel and the center panel.

2. A medical treatment facility gown, comprising:
   a urine catheter pocket affixed to a surface of the gown facing an interior of the gown when the gown is in a closed position;
   a fastener affixed to the gown surface, said fastener configured to secure a urine catheter bag to the gown surface within the urine catheter pocket;
   a left panel;
   a right panel; and
   a center panel positioned between the left panel and the right panel;
   wherein the urine catheter pocket and the fastener are affixed to the gown surface along a seam between one of the left panel or the right panel and the center panel.

3. The medical treatment facility gown of claim 2, wherein said fastener is configured to loop around a hook attached to a urine catheter bag received within an opening of the pocket along the surface and positioned in the urine catheter pocket, and wherein said fastener is a pair of ties affixed to the gown surface above the urine catheter pocket and wherein said pair of ties is configured to self-fasten upon looping around the hook of the urine catheter bag, to prevent the urine catheter from collapsing and to prevent the urine backflow out of the urine catheter bag and to conceal the catheter bag within the catheter pocket.

4. The medical treatment facility gown of claim 3, wherein said fastener is configured to loop around the hook of the urine catheter bag to secure the catheter bag to the gown surface above the catheter pocket.

5. The medical treatment facility gown of claim 4, wherein the catheter pocket is centered at the seam.

6. The medical treatment facility gown of claim 3, wherein said pair of ties is configured to fasten around the hook of the urine catheter bag above a threshold location, to prevent backflow of urine out of the urine catheter bag.

7. The medical treatment facility gown of claim 3, wherein the catheter pocket is affixed at a horizontal position along the surface of the gown, said horizontal position selected to be out of a path of motion of a leg of a patient wearing the gown while walking.

8. The medical treatment facility gown of claim 3, wherein the ties are configured to loop around the urine catheter bag hook and tie to one another, to secure the urine catheter bag along the surface of the gown above the urine catheter pocket, to prevent the urine catheter bag from collapsing and to prevent the urine backflow.

9. The medical treatment facility gown of claim 4, further including a respective surgical drain pocket affixed to the right panel of the gown surface and to the left panel of the gown surface, said respective surgical drain pocket configured to hold drains and tubing based on a location of a surgery performed on a patient.

10. The medical treatment facility gown of claim 4, further including:
    a first telemetry pocket affixed to the gown, and configured to hold a telemetry monitor, wherein said first telemetry pocket is concealed upon folding the right panel over the left panel when the gown is worn in a forward orientation; and a second telemetry pocket affixed to the center panel of the gown, and configured to hold the telemetry monitor, wherein said second telemetry pocket is visible when the gown is worn in a reverse orientation.

11. The medical treatment facility gown of claim 2, wherein said urine catheter pocket has an expandable side including accordion foldings along the expandable side, such that a volume of the urine catheter pocket is expandable as the urine catheter bag is filled, to prevent a constriction of the urine catheter bag and a backflow of urine.

12. The medical treatment facility gown of claim 4, including a plurality of side ties along an outer edge of the left panel and the right panel, such that upon wearing the gown, and folding the right panel over the left panel, the side tides of the right panel are tied to the side ties of the left panel along a side of a patient wearing the gown.

13. The medical treatment facility gown of claim 3, including a plurality of snaps along a top portion of the gown to form a plurality of openings, where each opening is formed between consecutive snaps, and wherein said snaps are configured such that an IV tubing is passed through at least one of the openings and inside the gown.

14. The medical treatment facility gown of claim 4, wherein said left and right panel have a respective upper edge that slants downward from the center panel in an outward direction when the gown is in an open position; and wherein upon folding the right panel over the left panel such that the gown is in the closed position, said upper edge of the left panel and the right panel form a V-shaped neck opening for a patient wearing the gown.

15. The medical treatment facility gown of claim 4, wherein upon folding the right panel over the left panel such that the gown is in the closed position, said gown is partially opened from the closed position by unfolding the right panel and the left panel to expose a front portion of a patient wearing the gown to perform treatment on the front portion of the patient without removing the gown from the patient.

* * * * *